(12) United States Patent
Baller et al.

(10) Patent No.: US 7,560,070 B1
(45) Date of Patent: Jul. 14, 2009

(54) CANTILEVER SENSORS AND TRANSDUCERS

(75) Inventors: Marko K. Baller, Santa Barbara, CA (US); Juergen Fritz, Karlsruhe (DE); Christoph Gerber, Richterswil (CH); James Gimzewski, Santa Monica, CA (US); Hans Peter Lang, Reinach (CH)

(73) Assignees: International Business Machines Corporation, Armonk, NY (US); Universitat Basel (CH)

( * ) Notice: Subject to any disclaimer, the term of this patent is extended or adjusted under 35 U.S.C. 154(b) by 602 days.

(21) Appl. No.: 10/129,254

(22) PCT Filed: Oct. 16, 2000

(86) PCT No.: PCT/IB00/01472

§ 371 (c)(1),
(2), (4) Date: Oct. 4, 2002

(87) PCT Pub. No.: WO01/33226

PCT Pub. Date: May 10, 2001

(30) Foreign Application Priority Data

Nov. 3, 1999 (EP) .................................. 99121790

(51) Int. Cl.
*G01N 33/00* (2006.01)
(52) U.S. Cl. .................. 422/50; 422/68.1; 422/83; 73/1.01; 73/1.02; 436/43; 436/63
(58) Field of Classification Search .................. 422/50, 422/68.1, 83; 73/1.01, 1.02; 436/43, 63
See application file for complete search history.

(56) References Cited

U.S. PATENT DOCUMENTS 4,549,427 A  10/1985  Kolesar (Continued)

FOREIGN PATENT DOCUMENTS

EP  0 711 410 B1  7/1993

(Continued)

OTHER PUBLICATIONS

"Dynamic Micromechanics on Silicon:" Techniques and Devices. Kurt E. Petersen. IEEE Transactions on Electron Devices, vol. Ed-25. No. 10, pp. 1241-1250, Oct. 1978.

(Continued)

*Primary Examiner*—Sam P Siefke
(74) *Attorney, Agent, or Firm*—Scully, Scott, Murphy & Presser, P.C.; Vazken Alexanian (57) ABSTRACT

Sensor system (70) for detecting a target substance in a reference liquid, comprising a measurement cantilever (71) being functionalized by application of a first coating to one of the measurement cantilever's surfaces, whereby this first coating is sensitive to the target substance. In addition, the system (70) comprises a reference cantilever (72) with a reference coating on one of the reference cantilever's surfaces, whereby this reference coating is less sensitive to the target substance than the first coating. Both cantilevers are arranged such that they can be exposed in a reference step to the reference liquid and in a detection step to the reference liquid with the target substance. A detector unit (73, 74, 83) is employed for determining the difference in the deflection of the measurement cantilever (71) and the reference cantilever (72) during the reference step and the detection step.

17 Claims, 9 Drawing Sheets

U.S. PATENT DOCUMENTS

| | | | |
|---|---|---|---|
| 5,445,008 A * | 8/1995 | Wachter et al. | 73/24.06 |
| 5,719,324 A * | 2/1998 | Thundat et al. | 73/24.01 |
| 5,737,086 A | 4/1998 | Gerber et al. | 356/432 |
| 5,807,758 A | 9/1998 | Lee et al. | 436/526 |
| 5,837,196 A * | 11/1998 | Pinkel et al. | 422/55 |
| 5,837,832 A * | 11/1998 | Chee et al. | 536/22.1 |
| 6,016,686 A | 1/2000 | Thundat | |
| 6,054,277 A * | 4/2000 | Furcht et al. | 435/6 |
| 6,096,559 A * | 8/2000 | Thundat et al. | 436/147 |
| 6,203,983 B1 * | 3/2001 | Quate et al. | 435/6 |
| 6,221,586 B1 * | 4/2001 | Barton et al. | 435/6 |
| 6,269,685 B1 * | 8/2001 | Oden | 73/54.23 |
| 6,289,717 B1 * | 9/2001 | Thundat et al. | 73/23.2 |
| 6,575,020 B1 * | 6/2003 | de Charmoy Grey et al. | 73/54.23 |
| 2002/0137084 A1 * | 9/2002 | Quate et al. | 435/6 |
| 2003/0154771 A1 * | 8/2003 | de Charmoy Grey et al. | 73/53.01 |
| 2003/0222232 A1 * | 12/2003 | Welland et al. | 250/573 |

FOREIGN PATENT DOCUMENTS

| | | |
|---|---|---|
| WO | WO 97/09584 | 3/1997 |
| WO | WO 98 50773 | 11/1998 |
| WO | WO 01/14539 | 3/2000 |
| WO | WO 00/58729 | 10/2000 |

OTHER PUBLICATIONS

"An Artificial Nose Based On a Micromechanical Cantilever Array". H.P. Lang. et al. Analytica Chimica Acta. vol. 393, No. 1-3. Jun. 30, 1999 pp. 59-65.

"A High-Sensitivity Micromachined Biosensor". David R. Baselt. et al. Proceedings of the IEEE. vol. 85. No. 4. pp. 672-680. Apr. 1997.

"Discrimination of DNA Hybridization Using Chemical Force Microscopy", Laura T. Mazzola. et al. Biophysical Journal. vol. 76.. Jun. 1999. pp. 2922-2933.

"Biosensor Based on Force Microscope Technology", David R. Baselt, et al. J.Vac. Sci. Technol. 14(2), Mar./Apr. 1996, pp. 789-793.

"Translating Biomolecular Recognition into Nanomechanics", J. Fritz. et al. Science. vol. 288. pp. 316-318. Apr. 14, 2000.

* cited by examiner

CANTILEVER SENSORS AND TRANSDUCERS

TECHNICAL FIELD

The invention concerns a new class of cantilever-based sensors and systems that transduce a molecular recognition, chemical affinity, or physical property into a mechanical response.

BACKGROUND OF THE INVENTION

The development of scanning tunneling and atomic force microscopes has led to various kinds of applications. Examples of these applications are: scanning probe storage systems, e.g. storage systems making use of parallel local probes, scanning probe lithography systems, test equipment comprising a scanning probe or array of probes, atomic resolution, high throughput inspection systems, and scanning probe system used for the structuring of surfaces such as semiconductor chips and the like. All these systems have in common that they comprise one or more cantilevers.

Increasing efforts have been put into the development of cantilever-based sensors for the detection of physical phenomena and bio/chemical reactions.

Examples are the calorimetric sensor, also referred to as chemical nose, described in European Patent EP 711410 B1, or the spectroscopic measurement system described in U.S. Pat. No. 5,737,086.

The international application with publication no. WO 98 50773 describes a biosensor that includes a cantilever microbeam which responds to a chemical stimulus, binding event or mass loading with an electrical output. The microbeam is formed using a series of microfabrication processes, in the micrometer to millimeter size range and using thin deposition of piezoelectric materials. It is further described that a reference sensor, which lacks a biomolecular recognition surface, defines the baseline or index resonant frequency of the beam structure(s). A second sensor (test sensor) containing the specific biomolecular recognition surface is oscillated in a same fluid environment, is permitted to react with the cognate analyte, through a mass loading event. The consequent resonant frequency of the test is measured.

U.S. Pat. No. 5,807,758 describes a method and apparatus for detecting a target species. The target molecule may be in liquid phase (in solution) or (for some embodiments of the invention) in vapor phase. A sensor according to the invention monitors whether a target species has selectively bound to groups on the cantilever surface by monitoring the displacement of the cantilever, and hence the force acting on the cantilever. This force acting on the cantilever arises from the force acting on a structure that moves in electric or magnetic field, and that may be selectively bound to the cantilever. In the case of target species having a sufficiently large net electric charge or dipole moment, the target species itself may serve as the structure that moves in an electric field. More typically however, separate modified structures, such as modified magnetic beads or modified beads having a net charge or a dipole moment, will, when selectively bound to the cantilever, exert a force on the cantilever that relates to the presence of the target species.

In the article 'An artificial nose based on a micromechanical cantilever array' by LANG H. P. ET AL. In ANALYTICAL CHIMICA ACTA, vol. 393, no. 1-3, 30 Jun. 1999, pages 59-65, ISSN: 0003-2670, is described a chemical sensor based on a micromechanical array of silicon cantilevers. The article gives an overview of operation principles of cantilever-based sensors. It is mentioned that the use of an array of cantilever sensors allows some of the cantilevers to serve as reference sensors, i.e. sensors that do not react with the analyte. Thus, a small sensor response can be extracted in noisy environment.

The article 'A high-sensitivity micromachined biosensor' by BASELT D. R. ET AL. in PROCEED. IEEE, vol 85, no. 4, 1997, pages 672-680, describes a Force Amplified Biological Sensor (FABS). Each FABS cell currently contains two side-by-side Helmholtz pairs, one for a signal cantilever and one for a reference. To cancel out noise from external vibrations, FABS uses a reference cantilever that is identical to the signal cantilever except that it does not have an antibody coating.

It is a disadvantage of known micromechanical sensor systems for recognition of target substances or detection of properties of liquids that the results are difficult to reproduce since there is a strong dependence on environmental parameters. It is another disadvantage of known schemes that they are very sensitive to temperature fluctuations, pH changes and the like. Recognition of atoms or molecules is thus very difficult if not impossible.

It is an object of the present invention to provide a scheme for the reliable recognition of atoms, molecules, cells, viruses, bacteria, or microorganisms in various environments.

It is an object of the present invention to provide a scheme for the reliable detection of properties of liquids in various environments.

It is an object of the present invention to provide a scheme for the automated control of liquid flows.

It is an object of the present invention to provide a scheme for the smart release or injection of a pharmaceutical substance or the like.

It is an object of the present invention to provide a scheme for transducing molecular recognition, chemical affinity, or physical property into a mechanical response.

SUMMARY OF THE INVENTION

The present invention concerns a scheme for detecting a target substance in a reference liquid. To achieve this a measurement cantilever which is functionalized by application of a first coating to one of the measurement cantilever's surfaces, whereby this first coating is sensitive to the target substance, and a reference cantilever with a reference coating on one of the reference cantilever's surfaces, whereby this reference coating is less sensitive to the target substance than the first coating, are employed. The measurement cantilever and the reference cantilever are exposed in a reference step to the reference liquid and in a detection step to the reference liquid with the target substance. A detector unit determines the difference in the deflection of the measurement cantilever and the reference cantilever during the reference step and the detection step.

A similar scheme can be used for the detection of the properties of a liquid.

The present invention also concerns a container comprising a bendable, micromechanical lid. This lid is connected to the container such that the container is open if the lid is bent. One of the lid's surfaces is functionalized by application of a coating which is sensitive to a target substance. If the lid is exposed to the target substance then forces in the lid automatically bend it such that the container opens.

The present invention also concerns a switch for use in a liquid flow system. The liquid flow system comprises a first pipe and a second pipe being connected to the first pipe at a branching point. A bendable, micromechanical lid is located at the branching point. This lid is functionalized by application of a coating to one of the lid's surfaces. This coating is sensitive to a target substance such that the exposure of the lid to a target substance generates forces in the lid which automatically bends it such that the cross-section at the branching point is changed in a manner to influence the liquid flow through the liquid flow system.

The present invention also concerns systems which transduce molecular recognition, chemical affinity, or physical property into a mechanical response. Such a system comprises at least one microstructured cantilever which has a functionalized surface. This surface is functionalized by application of a coating which is sensitive to a target substance (molecular recognition) or physical property of a target liquid. If the cantilever is exposed to the target substance or liquid, then forces in the cantilever automatically bend it. These forces occur between the cantilever's coating and the cantilever's surface. In other words, the cantilever transduces molecular recognition, chemical affinity, or physical property into a mechanical response (movement). The cantilever returns to its original position if the original situation is restored. This can for example be done by injecting a high concentration of urea, in the case of a DNA hybridization sensor, or some other liquid for other sensors. If the cantilever is now exposed to the target substance or liquid in an alternating manner, a flip-flop or bi-stable system can be built. Such systems can be used to build small micromechanical engines, pumps, containers, flow systems, and so forth.

It is an advantage of the present systems that they are very sensitive, suitable for mass production, and re-usable. In addition, the present systems show fast responses. Other advantages are either obvious for somebody skilled in the art or explicitly mentioned in the specification.

DESCRIPTION OF THE DRAWINGS

The invention is described in detail below with reference to the following schematic drawings. It is to be noted that the Figures are not drawn to scale.

DESCRIPTION OF PREFERRED EMBODIMENTS

Before different embodiments of the present invention are described, the basic elements of scanning probe systems, in accordance with the present invention, are addressed.

Cantilevers:

Cantilevers are well known elements which are easy to make. Existing semiconductor fabrication processes can be employed. In essence, the techniques of micromachining are employed to create discrete cantilevers and arrays of cantilevers. When dimensioning such cantilevers, one has to take into account specific parameters of the material used as substrate in which the cantilevers are formed. When properly designing a cantilever or a cantilever array, it can be mass-produced by batch processing at low cost with high yield.

Usually, cantilevers are made by etching away portions of a silicon substrate. This substrate is normally (100) or (111) oriented. (100) oriented silicon could for example be wet etched using ethyl diamine pyrocatechol or KOH solutions. Wet etching techniques are generally dependent on crystallographic orientation of the substrate, e.g. (100) oriented silicon shows a very low etch rate of the (111) plane, leading to a good etch stop along the (111) axis which generates well defined etch planes with 54.7° angles from (100). An alternative approach makes use of dry etching techniques, e.g. reactive-ion beam etching (RIE), chemically assisted ion beam etching, microwave assisted plasma etching, or inductively coupled plasma etching. Depending on process conditions, deep and anisotropic or isotropic structures can be obtained leading to excellent dimensional control. Masks can be employed to define the structures to be etched.

Likewise, cantilevers may be manufactured or modified using the focussed ion beam milling technique. In this technique, a pre-fabricated cantilever is enclosed in a vacuum chamber at a base pressure of about $2.3*10^{-6}$ mbar, for example. From an ion source, gallium (Ga) ions are accelerated by a high voltage (10-30 kV) and focussed on the target. A current of 12-12000 pA is used to erode the material at the target spot. The efficiency of the process can be enhanced by directing a stream of e.g. chloride molecules to a target area. The equipment for focussed ion beam milling is commercially available.

Focussed ion beam milling can also be used to modify conventional cantilevers. It is for example possible to form a smaller cantilever, or an array of cantilevers in a conventional cantilever.

The cantilevers used can have any shape that can be made using the above mentioned techniques. The cross-sectional shape perpendicular to the longitudinal axis of the cantilever could be rectangular, round, elliptical, or polygonal, for example.

Also suited for the fabrication of cantilevers are other semiconducting materials, like gallium arsenide, as reported in "Dynamic Micromechanics on Silicon: Techniques and Devices", K. E. Petersen, IEEE Transactions on Electronic Devices, Vol. ED25, No. 10, 1978, pp. 1241-1249. Also suited is Silicon Nitride ($SiN_x$).

Deflection Sensors:

In order to detect the deflection/bending of a cantilever, a deflection sensor is to be employed. The deflection of a cantilever is usually detected using optical or piezoresistive deflection sensors.

A piezoresistive resistor, for example, may be embedded at the fixed end of the cantilever arm. Deflection of the free end of the cantilever arm produces stress along the cantilever. That stress changes the resistor's resistance at the base of the cantilever in proportion to the cantilever's deflection. A resistance measuring apparatus is coupled to the piezoresistive resistor to measure its resistance and to generate a signal corresponding to the cantilever arm's deflection. As demonstrated for the first time in the copending patent application PCT/IB95/00724 filed on 1 Sep. 1995 such piezoresistive detectors can be formed in a constriction at the fixed end of the cantilever such that it undergoes even stronger stress.

An optical deflection sensor comprises a light source, e.g. a laser diode, and a photodetector. The light emitted by the light source is directed onto the cantilever and the photodiode is arranged such that reflected light is collected by it. A deflection of the cantilever leads to changed deflection of the light beams. This change in deflection can be detected by said photodiode and analyzed to obtain information as to amount of displacement of the cantilever.

Both detection approaches can be applied to the present invention.

Detector Circuitry:

Certain means, including detection circuitry, preamplifiers, and an appropriate wiring may be provided. To make these means one can employ existing tools and processes common to the semiconductor and solid-state industries. Depending on the specific application, miniaturization is mandatory to obtain short interconnections, high speeds, and reduced power consumption. Part or all of the detection circuitry may even be integrated into the cantilever chip.

The deflection sensors together with the detector circuitry is herein referred to as detector unit. The detector unit provides for data acquisition and analysis.

All embodiments of the present invention have in common that they comprise at least one microstructured cantilever or membrane built to operate as a bio/chemical sensor in liquids.

Figure 1A:
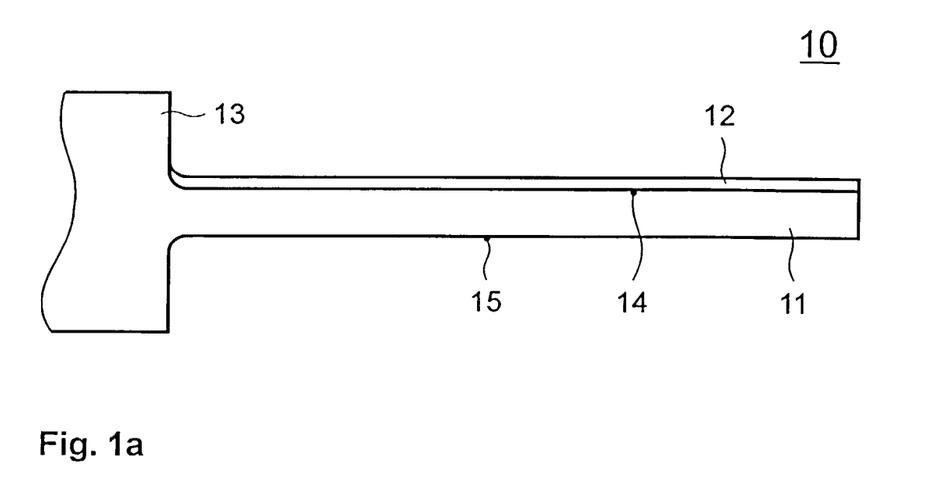
FIG. 1A is a schematic cross-section of a cantilever in accordance with the first embodiment of the present invention.
Figure 1B:
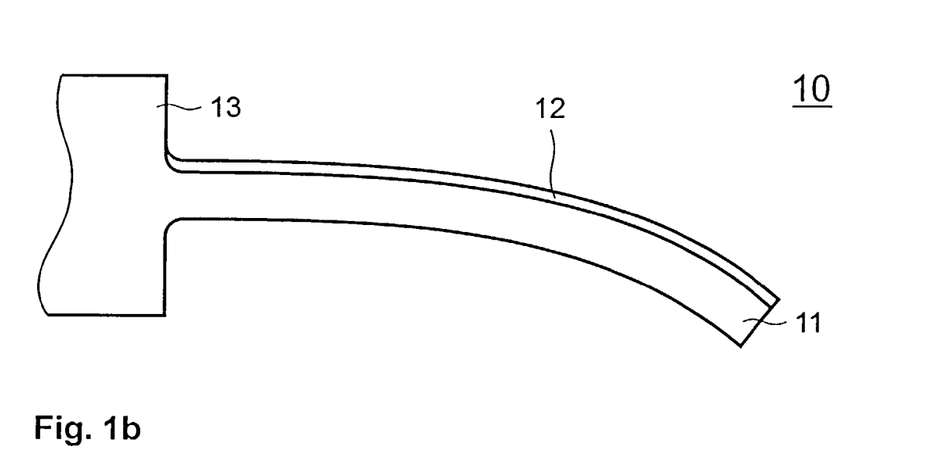
FIG. 1B is a schematic cross-section of a cantilever in accordance with the first embodiment of the present invention while being exposed to a target substance.

The present invention is now described in connection with a first embodiment. This embodiment is shown in FIGS. 1A and 1B. The cantilever structure 10 comprises a cantilever 11 and a mounting base 13. The mounting base 13 is usually carried by an cantilever holder (not shown).

Each cantilever 11 has two major surfaces, herein referred to as front-side 14 and back-side 15. In the present embodiment, the front-side 14 of the cantilever is covered by a coating 12. The cantilever 11 can be individually functionalized by application of the coating 12. For sake of simplicity, the coating 12 is shown to cover all of the front-side 14. It is also practical to apply a coating only to a portion of the cantilever's front-side 14 or back-side 15. The specific coating layer 12—which may be a single layer or a combination of several layers—transduces a physical process or a bio/chemical reaction into a micromechanical response (bending).

In general, a microstructured cantilever or membrane as described above consists of two different surfaces, a front- and a back-side, which have different affinities or interact differently when both are exposed to a target substance or a target liquid, or just one surface is exposed to the target substance or liquid. One surface of the cantilever or membrane has to be functionalized individually according to the analyte of choice, e.g., by proteins (antigen—antibodies, receptor—ligands, enzymes), oligonucleotides, self assembled monolayers (thiols), polymeric layers, cells or microorganisms.

A cantilever or membrane can be functionalized by (1) introducing it into a small container or channel of a microfluidic network filled with the liquid of choice, or (2) by evaporating or otherwise applying the coating to its surface.

If the microstructured cantilever 10 is exposed to a target substance, forces are generated which bend the cantilever 11 downwards, as shown in FIG. 1B, or upwards (not shown). The following mechanisms—or combination of these mechanisms—can lead to a bending of the cantilever: thermal effects, surface or interfacial stress generation, electrostatic interactions, steric or solvation effects, conformational changes of molecules or cells leading to an expansion or to changes of the elastic properties of the material on the cantilevers.

Please note that the microstructured cantilever 10 is a passive device. No actuators, excitation, or other means are required to generate the bending forces. The cantilever automatically bends if exposed to a target substance for which it was functionalized by application of an appropriate coating 12. According to the present invention static bending is detected rather than the dynamic (resonant) behavior.

The microstructured cantilevers or membranes can be functionalized such that they can be used to react, detect, or monitor physical parameters (herein referred to as properties) of a liquid, such as the temperature, refractive index, ion concentration or pH;

presence of a substance or material (herein referred to as target substance) in a liquid, especially by molecular recognition or binding of biomolecules with partners on the cantilever's coating;

physical or chemical properties of the material of or on the cantilever or interaction with the cantilever like surface charges or hydrophobicity, adsorption processes, pK values of self assembled monolayers or biomolecules, conformational changes of molecules on the surface, or responses of cells to different environments.

Figure 2A:
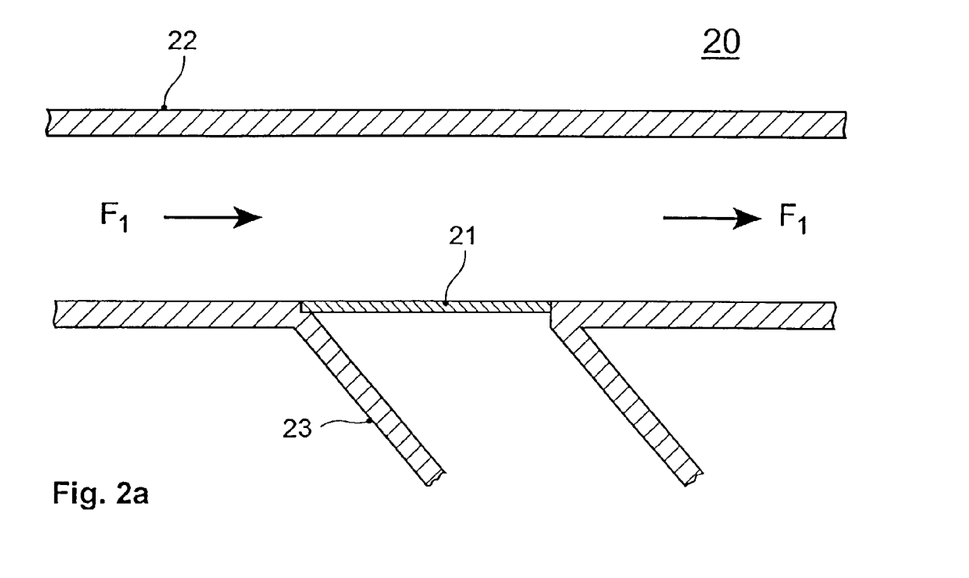
FIG. 2A is a schematic cross-section of a liquid flow system in accordance with an embodiment of the present invention.
Figure 2B:
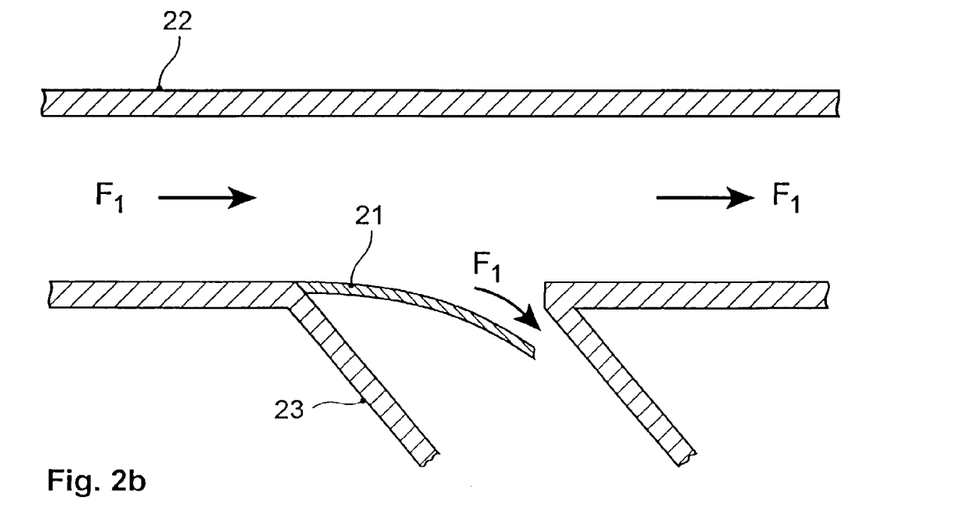
FIG. 2B is a schematic cross-section of a liquid flow system in accordance with an embodiment of the present invention where the lid is exposed to a target substance.

The bending of a microstructured cantilever or membrane caused by the interaction between the coating and the target substance can be used to open microfabricated doors or lids or to trigger valves of a microfluidic system. This allows to produce "intelligent" depots of pharmaceutical substances opening and closing at a defined value of, e.g., blood sugar, or in the presence of certain antibodies or viruses. A second embodiment of the present invention is illustrated in FIGS. 2A and 2B. This embodiment illustrates the use of a microstructured cantilever 21 in a liquid flow system 20. In the present embodiment, the microfabricated cantilever 21 serves as kind of a switch in the liquid flow system 20. The liquid flow system 20 comprises a first pipe 22 and a second pipe 23. The second pipe 23 is connected to the first pipe 22. The intersection of the first pipe 22 and second pipe 23 is referred to as branching point. The microfabricated cantilever 21 is arranged such that it closes the second pipe 23. In this state (see FIG. 2A), a liquid F1 flows through the pipe 22 from the left to the right. No liquid enters the second pipe 23 since its inlet is cover or closed by the cantilever 21.

The cantilever 21 is bendable. One of its surfaces (either the front- or the back-side) is functionalized by application of an appropriate coating (not shown in FIGS. 2A, 2B). This coating is sensitive to a target substance contained in the liquid F1. If we now assume that the target substance is added to the liquid F1, then the cantilever 21 bends, as illustrated in FIG. 2B. The bending of the cantilever 21 opens the second pipe 23. A certain percentage of the liquid F1 now flows from the first pipe 21 into the second pipe 23. In other words, the cantilever 21 acts as a switch between the two pipes. An exposure of the cantilever to the target substance generates forces which automatically bend it such that the cross-section at the branching point are changed in a manner to influence the liquid flow through the flow system 20. Note that the second pipe 23 remains open as long as the target substance is comprised in the liquid F1. If no more target substance is present in F1, or if its concentration falls below a detection threshold, the cantilever 21 moves back into its original position and the second pipe 23 is closed again.

Figure 3:
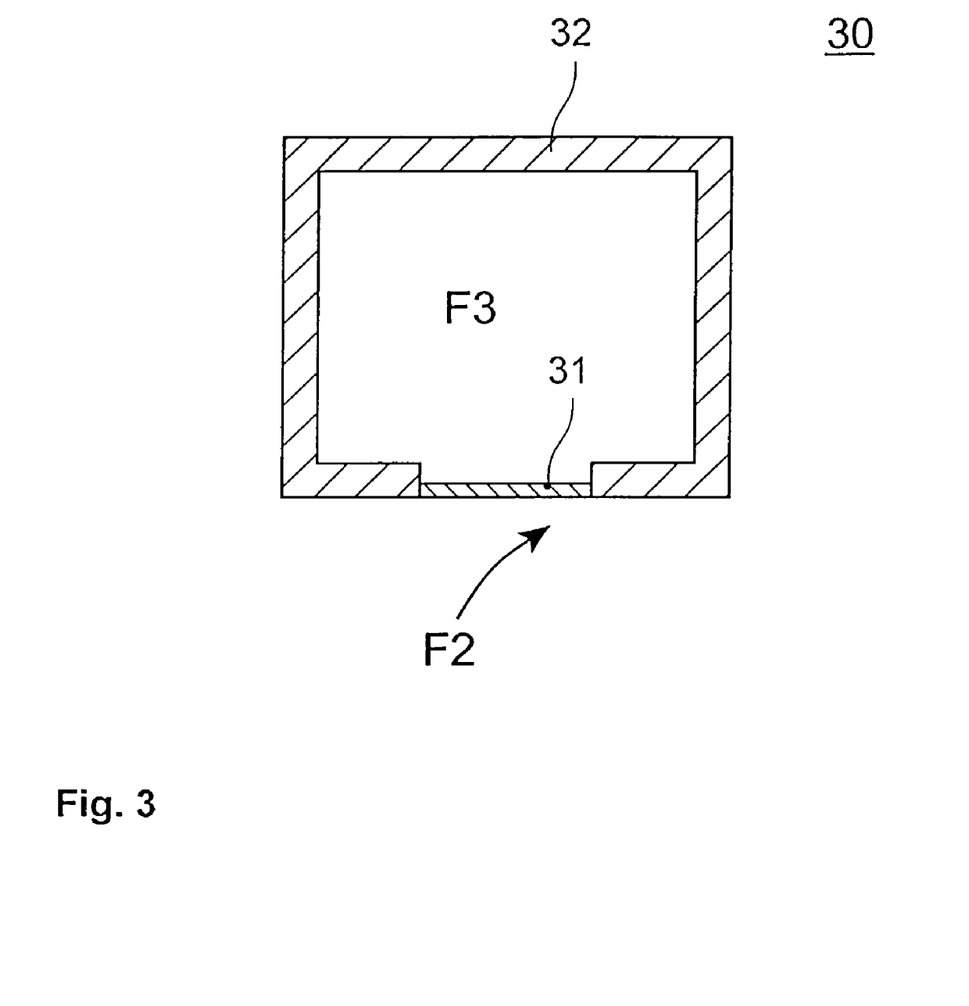
FIG. 3 is a schematic cross-section of a container in accordance with an embodiment of the present invention.

Yet another embodiment is illustrated in FIG. 3. The cross-section of a container system 30 is shown in this Figure. The container comprises walls 32 and a lid 31. A microstructured cantilever serves as lid 31. One of the lid's surfaces (either the front- or the back-side) is functionalized by application of an appropriate coating (not shown in FIG. 3) such that it is sensitized to a target substance or sensitized to certain properties of a target liquid. In the present embodiment, we assume that the cantilever is coated in a manner that it is sensitive to a difference in the pH of the liquid F2 outside the container 30 and a liquid F3 inside the container. This liquid F3 may contain a pharmaceutical substance (e.g., a drug). If the cantilever now detects a difference in the pH at its front-side (the surface facing the liquid F2) and its back-side (the surface facing the liquid F3), a force is generated which bends the cantilever 31. The bending of the cantilever 31 is not illustrated. As a result of the bending, the container 30 opens and an exchange/mixing between the liquids F2 and F3 takes place. As a result, the pH difference disappears and the container 30 closes again. Part of the liquid F3 was released into the liquid F2. This effect may be used to release small doses of a pharmaceutical substance into blood, for example.

Some embodiments are now illustrated where an array of at least two cantilevers is employed.

Such arrays consist of at least of two cantilevers one acting as an inert reference, the other as a sensing cantilever. Both cantilevers can be functionalized individually according to the analyte of choice, i.e. by proteins (antigen—antibodies, receptor—ligands, enzymes), oligonucleotides, self assembled monolayers (thiols), polymeric layers, cells or microorganisms. This can be done either by introducing the cantilevers in parallel into small containers or channels of a microfluidic network filled with the liquid of choice. The bending of the cantilevers is read out in parallel, e.g. by an optical beam deflection method using multiplexed light sources like an array of VCSELs (vertical cavity surface emitting laser). It is important that there always is a pair of corresponding cantilevers which have the same physical properties prior to the application of the coating. Ideally, the cantilevers are made at the same time using the same manufacturing steps.

Cantilever array-based systems can be built to operate as a bio/chemical sensor systems for use in liquids. Such sensor systems can be used to detect protein adsorption on cantilever surfaces, pH-changes of solution and molecular recognition by a static cantilever bending. A modified commercial AFM head and a liquid cell may be used to build a sensor system.

A example of a sensor system 40 is given in FIGS. 4A-4D. The present sensor system 40 is designed to detect a single stranded DNA (ssDNA) strand (referred to as target substance) in a reference liquid. The system 40 comprises a measurement cantilever 41 which is functionalized by application of a first coating to one of the measurement cantilever's surfaces. In the present example the first coating is applied to the front-side (top-surface) of the cantilever 41. This first coating is sensitive to a particular complementary DNA strand (target DNA strand). A reference cantilever 42 comprises a reference coating on one its top surfaces. This reference coating is less sensitive to the target DNA strand than the first coating. Both cantilevers are connected to a cantilever holder 43 for exposing the measurement cantilever 41 and the reference cantilever 42 in a reference step to a reference liquid and in a detection step to the reference liquid with the target substance. It is important that both cantilevers are identical with the exception of their functionalization. Furthermore, the sensor system 40 comprises a detector unit (not shown in FIGS. 4A-4C) for determining the difference in the deflection of the measurement cantilever 41 and the reference cantilever 42 during the reference step and the detection step. The bending of the cantilevers 41 and 42 can be detected by an optical read out technique consisting of two multiplexed VCSEL and one linear position sensitive detector.

Figure 4A:
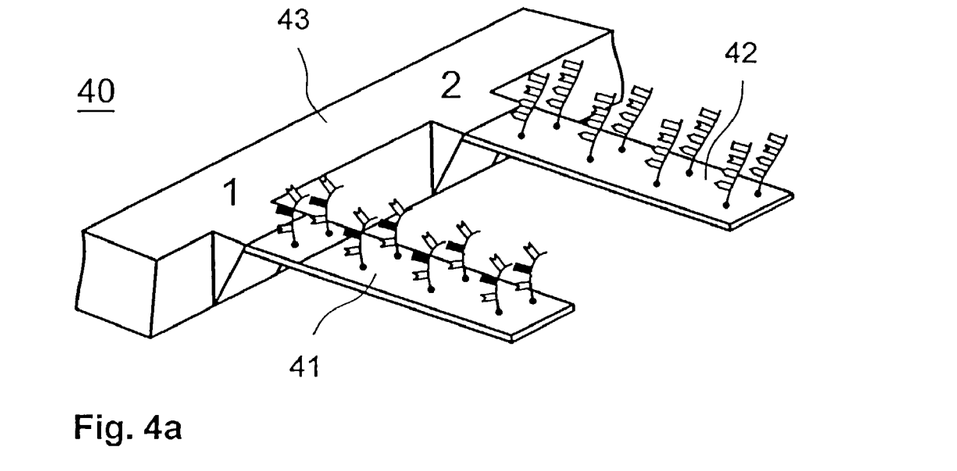
FIGS. 4A-4C are schematic cross-sections of an array-based sensor system in accordance with an embodiment of the present invention.

Here, both cantilevers 41 and 42 are functionalized by short strands of single-stranded DNA, so called oligonucleotides, modified by a thiol group at their 5' end. One cantilever is covered by a 12mer oligonucleotide, the other cantilever by a 16mer oligonucleotide, both with different sequences, so that the cantilever surfaces exhibit the same physical properties, and only differ in their base sequence, the genetical information of the oligonucleotides. The 12mer cantilever may serve as a reference cantilever for the 16mer cantilever, or vice versa.

Figure 4B:
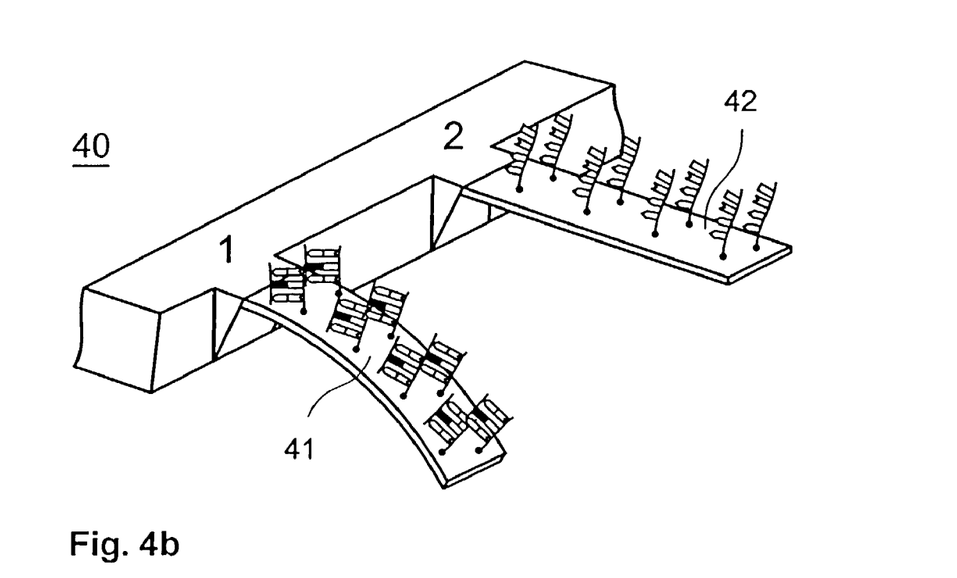

The sensor system 40 further comprises a liquid cell which allows the two cantilevers 41 and 42 to be exposed to a reference liquid and the target substance. By injecting the complementary strands of oligonucleotides in the liquid cell, base pairing, called hybridization, occurs and the complementary strands bind only to the cantilever 41 with the matching sequence. The cantilevers 41 bend away from the side where the hybridization occurs, as shown in FIG. 4B. The difference in bending between the two cantilevers 41 and 42 (here the signal in bending from the 12mer functionalized cantilever minus the signal from the 16 mer cantilever) is detected and recorded by the detector unit.

Figure 4C:
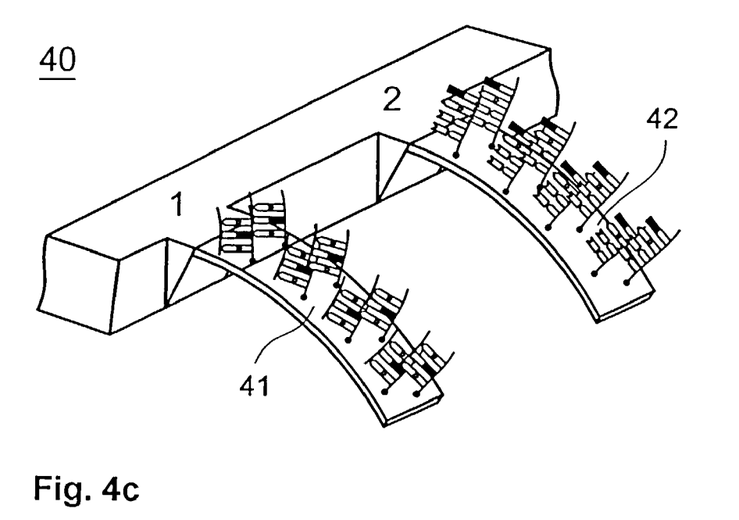
Figure 4D:
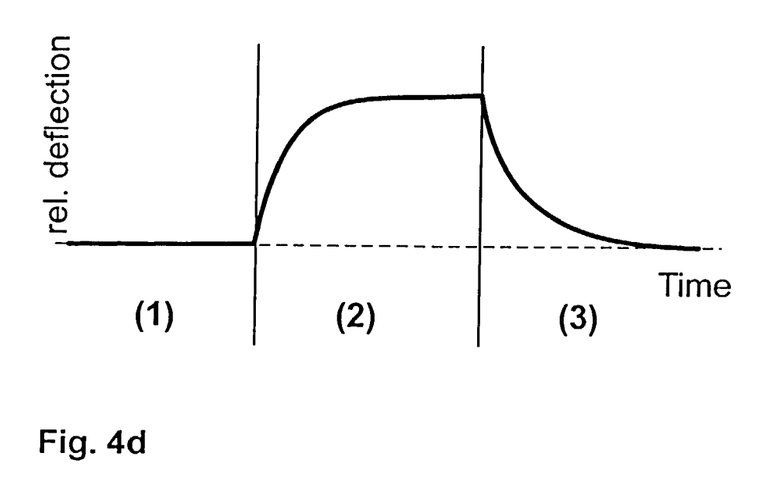
FIG. 4D is a schematic plot of the relative deflection of the two cantilevers of the array-based sensor system illustrated in FIGS. 4A-4C.

In FIG. 4B, first the complementary 12mer oligo was injected, and the output signal of the detecting unit goes up (see FIG. 4D). Then, after purging with a reference liquid, the complementary 16 mer was injected so that the cantilever 42 bends down as well (see FIG. 4C). This means that the output signal of the detecting unit goes down (see FIG. 4D). The relative deflection between the two cantilevers 41 and 42, i.e. the difference in bending, is plotted in FIG. 4D. This difference signal is the output signal of the detector unit. The detector system described above allows the recognition of molecules, e.g. bio-molecules such as DNA.

Figure 5:
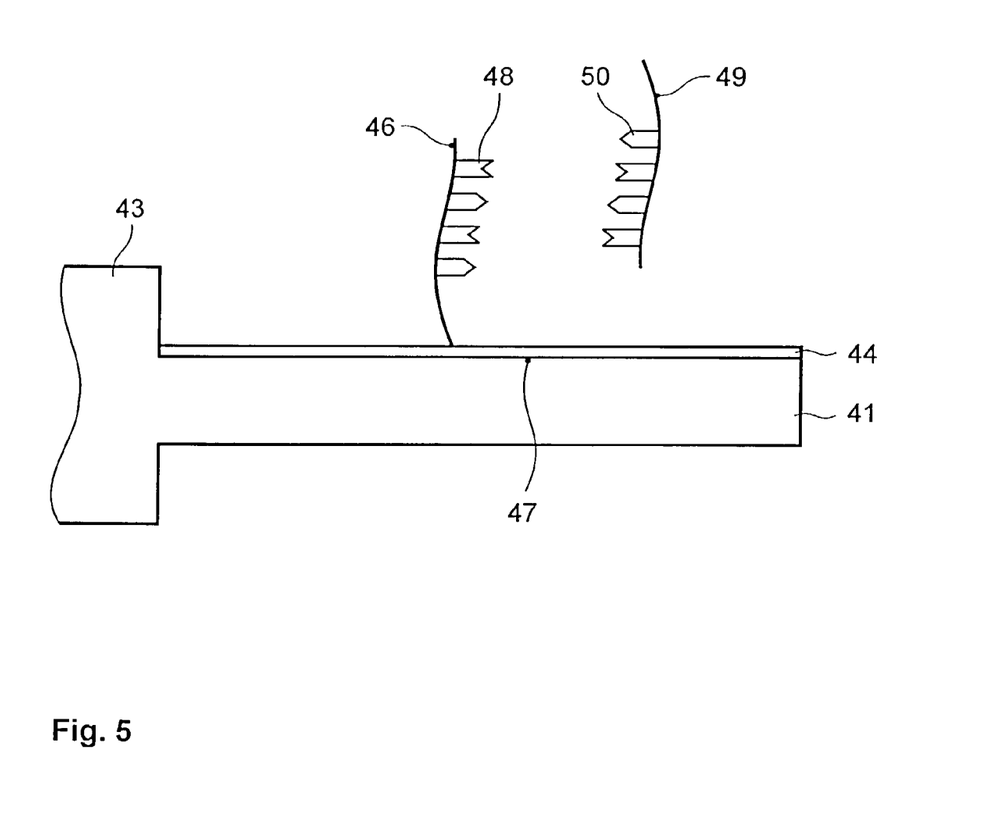
FIG. 5 is a schematic cross-section of a cantilever in accordance with an embodiment of the present invention.

For the recognition of single stranded DNA (ssDNA), a silicon cantilever array is well suited. Typical dimensions of the individual cantilevers are: a thickness between 0.1 micron and 10 micron; a length between 50 micron and 1000 micron; a width between 10 micron and 500 micron. Well suited for the recognition of DNA strands is a layered coating, illustrated in FIG. 5, which comprises, from the cantilever surface 47 up, a metal layer 44 (e.g., a gold layer) which allows thiol-modified short strands of single-stranded DNA 46, so called oligonucleotides, to be linked to the cantilever 41. The bases 47 of the single-stranded DNA form base-pairs with the bases 50 of their complementary DNA strand 49 during a hybridization process.

The sensor system 40 allows to monitor the molecular recognition by static cantilever bending. In the present embodiment, the bending of the cantilevers is dependent on the concentration of complementary oligonucleotides. In the current setup, sensitivity is better than $10^9$ molecules which correspond to a complete surface coverage. The time dependent bending signal can be fitted by a Langmuir adsorption kinetic. Further on, the system 40 is able to detect strands of same length but with different base sequence and even single base mismatches in a oligonucleotide sequence. This allows detection of genetic variations (such as mutation analysis, single nucleotide polymorphism) by means of sequencing by hybridization.

The base pairing can be chemically broken by injecting high concentrations e.g. of urea into the liquid cell. Then, the experiment can be repeated with the same sensor system 40.

As mentioned above, one side of the Si cantilever is covered by metal layer. The thickness of this layer can be between 1 nm and 500 nm. Well suited is a gold layer with a thickness of 20 nm to increase their reflectivity for the optical readout. The metal layer can be applied by electron beam evaporation, for example. The other layers can be spray-coated onto the cantilever, for example.

Each side of both cantilevers can be individually functionalized by either thiol- or silane chemistry. By using two or more cantilevers in parallel one of the cantilevers can be operated as a reference. This is especially important for measuring static deflections of cantilevers in liquids, because small changes in temperature and refractive index of the liquid (depending, e.g., on pH or ion concentration) influence dramatically the signal (e.g. 100 nm deflection per ° C., or several 10 nm per pH unit). These effects can be canceled out by evaluating the differential signal between a specifically sensitized cantilever and an inert reference cantilever.

The system illustrated in FIGS. 4A-4C can also be used to detect or recognize RNA.

In another embodiment, one cantilever is now functionalized by an inert alkylthiol ($CH_3$) and the other cantilever by a carboxythiol (COOH), which can be protonated/deprotonated due to pH of the solution (0.1 M phosphate buffer). At low pH, the COOH-terminated cantilever surface is uncharged but gets more negatively charged as more deprotonated $COO^-$ groups build up at higher pH. This bends the cantilever away from the charged thiollayer. Such a sensor system can be used as a microfabricated, highly sensitive and local pH-meter. The bending signal decreases for mixed thiol layers with a reduced number of carboxy groups on the cantilever surface. The bending of the carboxythiol-covered cantilever increases by adding ions in solution. This indicates that electrostatic repulsion and screening of surface charges by counter ions are not the only causes for cantilever bending.

Figure 6:
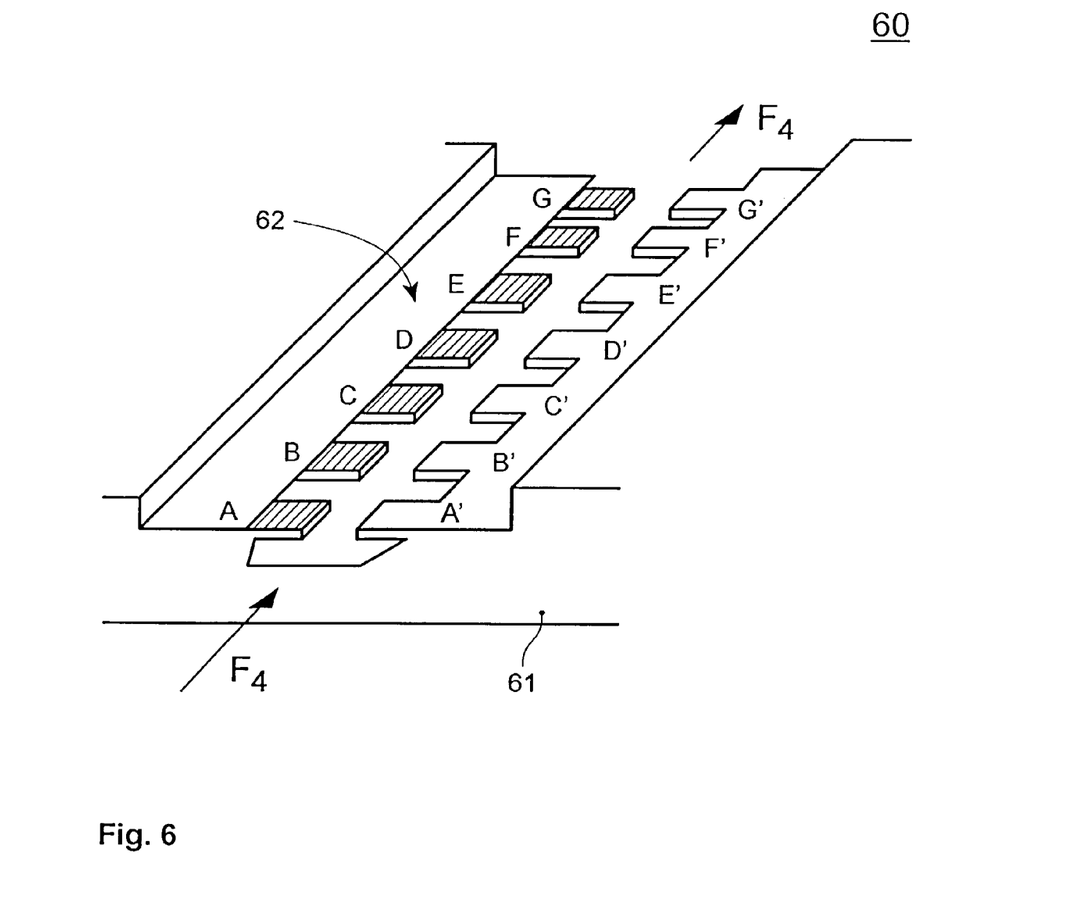
FIG. 6 is a schematic view of an array-based sensor system in accordance with an embodiment of the present invention.

Another embodiment is shown in FIG. 6. The sensor system 60 comprises an array of 7 measurement cantilevers (A through G) and 7 opposite reference cantilevers A' through G'). The array's mounting base 61 serves as cantilever holder is structured such as to provide a channel for the guiding of a liquid flow F4. The liquid F4 flows along the channel 62 in a manner that all cantilevers are exposed to the liquid. In the present case, each cantilever comprises a piezoelectric detector which provides a read-out signal to a detection circuitry. The detection circuitry receives signals from each cantilever and generates 7 output signals. These 7 output signals are the difference signals of the signals provided by the cantilever pairs A-A', B-B', . . . , G-G'. The detection circuitry may be connected to a computer system for subsequent processing of the 7 output signals.

Figure 7:
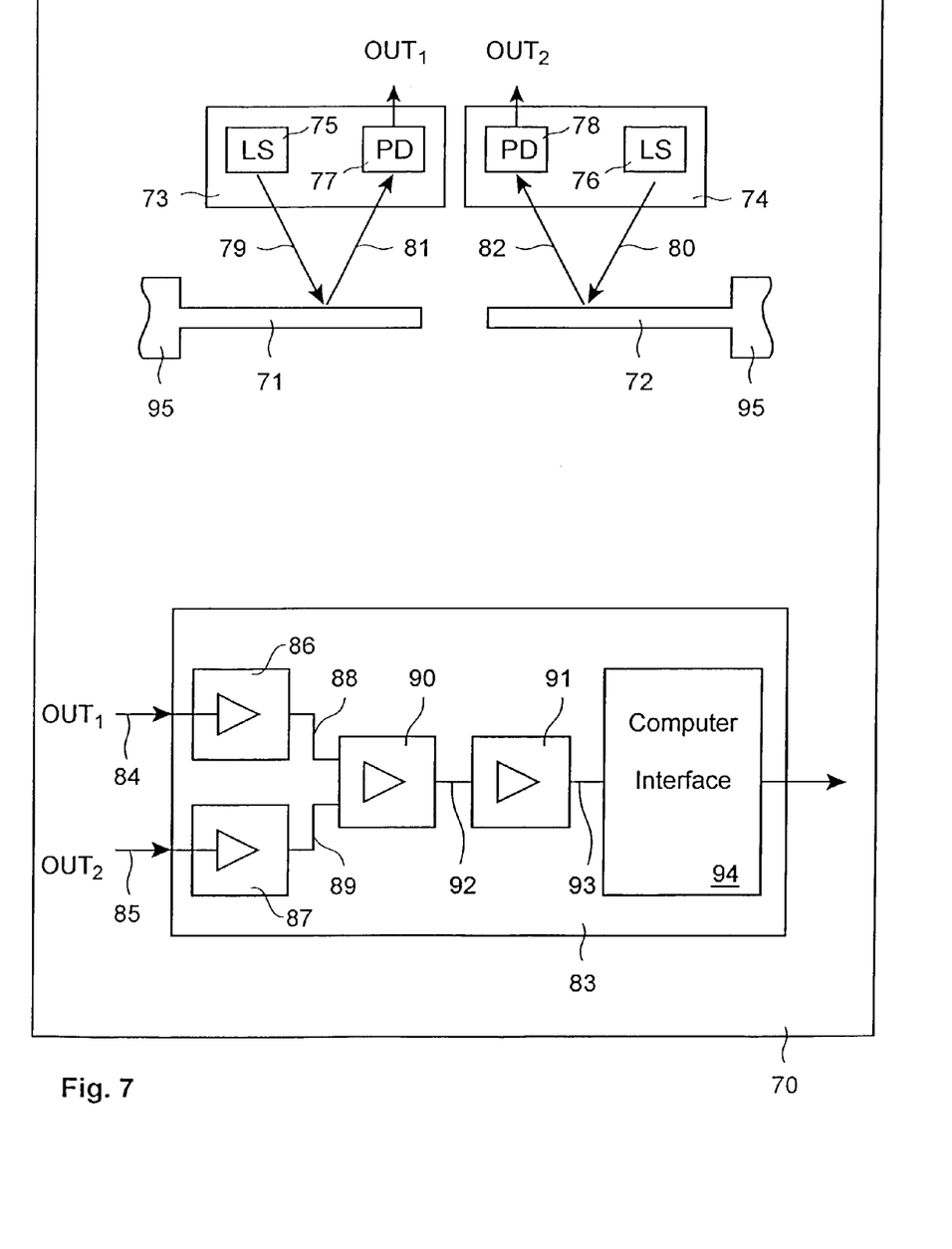
FIG. 7 is a schematic view of another array-based sensor system in accordance with an embodiment of the present invention.

The block diagram of a sensor system with two cantilevers 71, 72 and a typical detection unit is illustrated in FIG. 7. In the present embodiment there is one optical deflection sensor system 73 (74) per cantilever 71 (72). Each such deflection sensor system 73 (74) comprises a light source 75 (76), e.g. a laser diode, and a photodetector 77 (78). The light 79 (80) emitted by the light source 75 (76) is directed onto the cantilever 71 (72) and the photodiode 77 (78) is arranged such that reflected light 81 (82) is collected by it. A deflection of the cantilever 71 (72) leads to changed deflection of the light beams 81 (82). This change in deflection can be detected by said photodiode 77 (78) which produces an output signal OUT1 (OUT2). These output signals OUT1 and OUT2 (photo currents) are analyzed by a unit 83 to obtain information as to amount of relative displacement of the two cantilevers 71 and 72.

The unit 83 has two inputs 84 and 85 at which the photo currents of the photodiodes 77, 78 are received. The blocks 86 and 87 transform the photo currents into voltages 88, 89. Building block 90 generates the difference between the two voltages 88, 89. An optional amplifier 91 is employed to amplify the difference signal 92. In the present example, the resulting signal 93 is fed to an interface card 94 through which the unit 83 is connected to a computer (not shown). The computer records the resulting signal for further processing. There may also be a feedback loop between the deflection sensor systems 73, 74 and the unit 83 and/or computer. The deflection sensor systems 73 and 74 together with the unit 83 are herein referred to as a detection unit.

Figure 8:
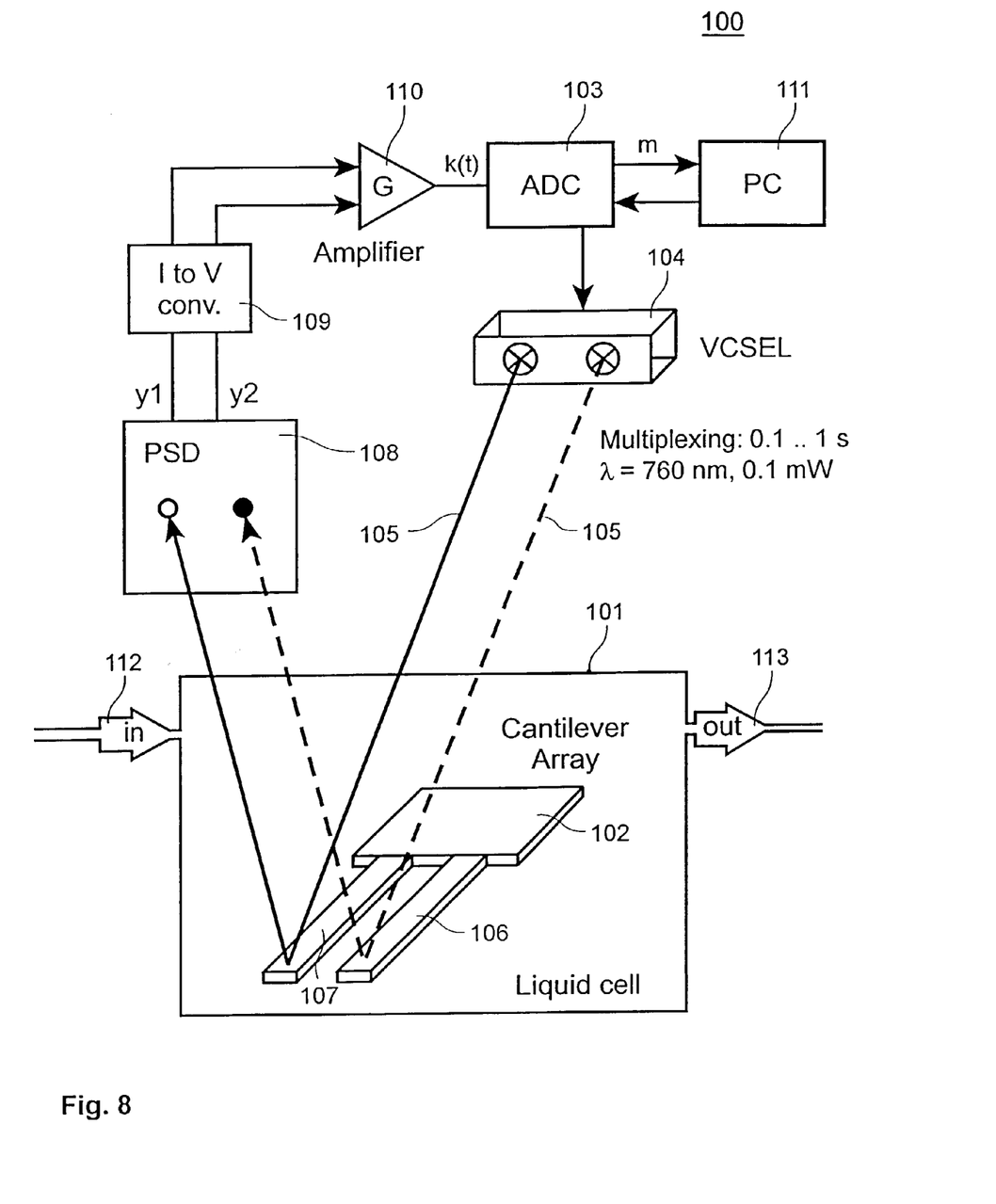
FIG. 8 is a schematic block diagram of another embodiment of the present invention.

Another embodiment of the present invention is illustrated in FIG. 8. This Figure illustrates the schematic setup of sensor system 100 with a liquid cell 101 housing a cantilever array 102. The liquid cell 101 has an input 112 and output 113. The system's detector unit comprises an acquisition and control unit 103 (ADC) that switches light sources 104 (in the present embodiment a VCSEL array) on and off via a time-multiplexing scheme. A typical VCSEL has a wavelength of 760 nm and an output power of about 0.1 mW. The laser light 105 might be multiplexed at a rate between 0.1 and 1 s. The laser light 105 from a VCSEL array 104 is directed via focusing optics (not shown) onto the apex of the cantilevers 106, 107 of the array 102, then reflected and collected by a linear position sensitive detector 108 (PSD). This PSD 108 generates photo currents y1 and y2 for cantilevers 107 and 106, respectively. The photo currents y1 and y2 from opposing electrodes are converted into voltages by an I-to-V converter 109. The output voltages V1 and V2 are then amplified by an amplifier 110 (amplification factor G). The acquisition and control unit 103 then processes the amplifier's output signal k(t). The ADC 103 may for example comprise an analog-to-digital converter for generating a digital output signal m. The signal m is then forwarded to a personal computer 111 (PC) where it may be processed and recorded, for example. The processing of the recorded information may be performed off-line on the personal computer 111.

The functionalized/sensitized cantilever arrays are reusable at least for 10 times, and can be stored before use for at least several days.

In the future the number of cantilevers per array can be increased and/or three-dimensional instead of the present two-dimensional cantilever arrays can be used. Furthermore, the cantilevers can be further miniaturized. This leads to new classes of nanomechanical DNA chips, with all the applications of such chips. The present embodiment have a clear advantage of known recognition schemes which require labeling (e.g. by fluorophores). According to the present invention, labeling is not needed since bio-molecules are detected via the static bending of cantilevers.

The detector unit may allow the differential signal to be recorded. The differential signal from two cantilevers is measured to cancel out parasitic signals or a background, e.g. bending through temperature changes, signals from refractive index changes or reactions and adsorption going on identical surfaces of the cantilevers.

A cantilever array in accordance with the present invention can be used as kind of "biomolecular tweezer". Bio-molecules, especially long strands of DNA can be detected by cantilever bending and afterwards the cantilever can be broken out of the array. The molecules can be removed from their binding partners on the surface and can be further analyzed by biochemical methods.

Depending on implementation details, the inventive approach allows detection of molecules, cells, viruses, bacteria, microorganisms, atoms, ions, protons, and probably even electrons.

Systems according to the present invention can be used for process and quality control, disposable bio-sensing for medical analysis, fragrance design, oenology, and as sensing devices for liquid analytes.

A sensor system according to the present invention may be used to build a pH-meter. In this case, the measurement cantilever would comprise a pH-sensitive coating and the reference cantilever a pH-insensitive coating.

The herein described systems can be used in-vitro and/or in-vivo.

The invention claimed is:

1. Sensor system (70) for detecting a target nucleotide strand in a reference liquid, comprising
    a measurement cantilever (71) being functionalized by application of a first coating to one of the measurement cantilever's surfaces, whereby this first coating comprises a first oligonucleotide that hybridizes to the target nucleotide strand,
    a reference cantilever (72) with a reference coating on one of the reference cantilever's surfaces, whereby this reference coating comprises a second oligonucleotide that does not hybridize to the target nucleotide strand, wherein the surfaces of the measurement cantilever (71) and the reference cantilever (72) exhibit the same physical properties and differ only in the base sequences of the first and second oligonucleotides,
    a cantilever holder (95) for exposing the measurement cantilever (71) and the reference cantilever (72) in a reference step to the reference liquid and in a detection step to the reference liquid with the target nucleotide strand,
    a detector unit (73, 74, 83) for determining the difference in static deflection of the measurement cantilever (71) and the reference cantilever (72) during the reference step and the detection step,
    wherein the difference in static deflection of the measurement cantilever (71) and the reference cantilever (72) is indicative of the target nucleotide strand in the reference liquid.

2. Sensor system for detecting a property of a target liquid, comprising
    a measurement cantilever being functionalized by application of a first coating to one of the measurement cantilever's surfaces, whereby this first coating comprises a first oligonucleotide that is sensitive to the target liquid,
    a reference cantilever with a reference coating on one of the reference cantilever's surfaces, whereby this reference coating comprises a second oligonucleotide that is less sensitive to the target liquid than the first coating, wherein the surfaces of the measurement cantilever and the reference cantilever exhibit the same physical properties and differ only in the base sequences of the first and second oligonucleotides,
    a cantilever holder for exposing the measurement cantilever and the reference cantilever to the target liquid while the property of the target liquid changes,
    a detector unit for determining the difference in static deflection of the measurement cantilever and the reference cantilever while the property of the target liquid changes,
    wherein the difference in static deflection of the measurement cantilever and the reference cantilever is indicative of the property of the target liquid.

3. Sensor system according to claim 1, whereby the coating comprises two or more layers.

4. Sensor system according to claim 1, whereby the coating comprises a metal layer.

5. Sensor system according to claim 1, whereby the coating comprises single stranded DNA.

6. Sensor system according to claim 1, whereby the coating comprises single stranded RNA.

7. Sensor system according to claim 1, whereby the measurement cantilever and the reference cantilever are individually functionalized by either thiol-chemistry or silane chemistry.

8. Sensor system according to claim 1, whereby the detector unit comprises an optical detection system or a piezoresistive detection system.

9. Sensor system according to claim 1, whereby the target nucleotide strand is a DNA strand complementary to said first oligonucleotide.

10. Sensor system according to claim 1, whereby the target nucleotide strand is a RNA strand complementary to said first oligonucleotide.

11. Method for detecting a target nucleotide strand in a reference liquid by means of a measurement cantilever being functionalized by application of a first coating to one of the measurement cantilever's surfaces, whereby this first coating comprises a first oligonucleotide that is sensitive to the target nucleotide strand, and a reference cantilever with a reference coating on one of the reference cantilever's surfaces, whereby this reference coating comprises a second oligonucleotide that is less sensitive to the target nucleotide strand than the first oligonucleotide, wherein the surfaces of the measurement cantilever and the reference cantilever exhibit the same physical properties and differ only in the base sequences of the first and second oligonucleotides, the method comprising the steps of:
    a. exposing the measurement cantilever and the reference cantilever to the reference liquid,
    b. measuring the deflection of the measurement cantilever and the reference cantilever,
    c. exposing the measurement cantilever and the reference cantilever to a reference liquid with the target substance,
    d. measuring static deflection of the measurement cantilever and the reference cantilever, determining the difference in deflection between step a. and step c,
    e. wherein the difference in static deflection between step a. and step c. is indicative of the target nucleotide strand in the reference liquid.

12. The method of claim 11, whereby step c. is carried out prior to step a.

13. The method of claim 11, whereby the step a. is carried out during system setup or initialization.

14. Sensor system according to claim 2, whereby the coating comprises two or more layers.

15. Sensor system according to claim 2, whereby the coating comprises a metal layer.

16. Sensor system according to claim 2, whereby the measurement cantilever and the reference cantilever are individually functionalized by either thiol-chemistry or silane chemistry.

17. Sensor system according to claim 2, whereby the detector unit comprises an optical detection system or a piezoresistive detection system.

* * * * *